US005763429A

United States Patent [19]
Bishop et al.

[11] Patent Number: 5,763,429
[45] Date of Patent: Jun. 9, 1998

[54] METHOD OF TREATING PROSTATIC DISEASES USING ACTIVE VITAMIN D ANALOGUES

[75] Inventors: Charles W. Bishop; Joyce C. Knutson; Richard B. Mazess, all of Madison, Wis.

[73] Assignee: Bone Care International, Inc., Madison, Wis.

[21] Appl. No.: 781,910

[22] Filed: Dec. 30, 1996

Related U.S. Application Data

[63] Continuation-in-part of Ser. No. 415,488, Apr. 3, 1995, Pat. No. 5,602,116, which is a continuation-in-part of Ser. No. 119,895, Sep. 10, 1993, Pat. No. 5,403,831, and a continuation-in-part of Ser. No. 486,387, Jun. 7, 1995, Pat. No. 5,674,859, which is a continuation-in-part of Ser. No. 265,438, Jun. 24, 1994.

[51] Int. Cl.$^6$ .................................................. A61K 31/59
[52] U.S. Cl. .............................. 514/168; 514/167; 552/653
[58] Field of Search .................................. 514/167, 168; 552/653

[56] References Cited

U.S. PATENT DOCUMENTS

| | | | |
|---|---|---|---|
| 2,383,446 | 6/1945 | Calcott et al. | 204/159 |
| 3,697,559 | 10/1972 | DeLuca et al. | 260/397.2 |
| 3,741,996 | 6/1973 | DeLuca et al. | 260/397.2 |
| 3,907,843 | 9/1975 | DeLuca et al. | 260/397.2 |
| 4,195,027 | 3/1980 | DeLuca et al. | 260/397.2 |
| 4,202,829 | 5/1980 | DeLuca et al. | 260/397.2 |
| 4,225,596 | 9/1980 | DeLuca et al. | 424/236 |
| 4,234,495 | 11/1980 | DeLuca et al. | 260/397.2 |
| 4,260,549 | 4/1981 | DeLuca et al. | 260/397.2 |
| 4,362,710 | 12/1982 | Watanabe | 424/14 |
| 4,508,651 | 4/1985 | Baggiolini et al. | 260/397.2 |
| 4,554,106 | 11/1985 | DeLuca et al. | 260/397.2 |
| 4,555,364 | 11/1985 | DeLuca et al. | 260/397.2 |
| 4,588,716 | 5/1986 | DeLuca et al. | 260/397.2 |
| 4,661,294 | 4/1987 | Holick et al. | 260/397.2 |
| 4,689,180 | 8/1987 | Deluca et al. | 260/397.2 |
| 4,866,048 | 9/1989 | Calverley et al. | 514/167 |
| 5,063,221 | 11/1991 | Nishii et al. | 514/167 |
| 5,104,864 | 4/1992 | DeLuca et al. | 514/167 |
| 5,157,135 | 10/1992 | Tsuji et al. | 514/167 |
| 5,403,831 | 4/1995 | DeLuca et al. | 514/167 |
| 5,602,116 | 2/1997 | Knutson et al. | 514/167 |

FOREIGN PATENT DOCUMENTS

| | | |
|---|---|---|
| A-877 356 | 10/1979 | Belgium . |
| 0197514 | 10/1986 | European Pat. Off. . |
| A-0 390 097 | 10/1990 | European Pat. Off. . |
| 0 562 497 A | 9/1993 | European Pat. Off. . |
| 8404527 | 11/1984 | WIPO . |
| WO 87/00834 | 2/1987 | WIPO . |
| WO 90/10620 | 9/1990 | WIPO . |

OTHER PUBLICATIONS

L.E. Reeve et al., "Biological Activity of 1 α–hydroxy Vitamin $D_2$ in the Rat" *Arch. Biochem. Biophys.* 186, 1, Feb. 1978, pp. 164–167.

Sjoden et al., "Effects of 1 $OHD_1$ on Bone Tissue" *Acta. Endocrinol.* (Copenh.) 16, 4, Aug. 1984, pp. 564–568.

N./ Brautbar, "Osteoporosis: Is $1,25–(OH_2)_2D_3$ of Value in Treatment?" *Nephron* 44, 1986, pp. 161–166.

*Physicians Desk Reference,* Edition 43, pp. 1746–1748.

Y. Tanaka et al., *Endocrinology,* 1973, 92; pp. 417–422.

O.H. Sorenson et al., *Clin. Endocrinol.,* 1977, 7, pp. 169S–175S.

V. Hoikka et al., *Acta. Med. Scand.,* 1980, 207, pp. 221–224.

Brown et al., *Lancet,* 1984, 1, pp. 1091–1093.

J. Podenphant et al., *Acta Med Scand.,* 1985, 218, pp. 329–333.

Caniggia et al., *Calif Tissue Int.,* 1986, 38, pp. 328–332.

Duda et al., *J. Clinic Invest.,* 1987, 79, pp. 1249–1253.

Sommerfeldt et al., *J. Nutr.,* 1983, 11, pp. 2595–2600.

Zerwebh et al., *J. Clin. Endocrinol. Metabol.,* 1985, 60, pp. 615–617.

Horst et al., *Anal. Biochem.,* 1981, 116, pp. 189–203.

Horst et al., *Biochem. J.,* 1982, 204, pp. 185–189.

Foldes et al., *Osteoporosis* 1987, C. Christianson et al. (eds.) Osteopress Aps, Copenhagen, pp. 971–973.

Guidelines for the Clinical Evaluation of Drugs Used in the Treatment of Osteoporosis , HEW (FDA) 80–3094, pp. 5–6 (1979).

J.A. Kanis et al., Guidelines for Clinical Trials in Osteoporosis, A Position Paper of the European Foundation for Osteoporosis, *Osteoporosis Int.,* 1991, 1, pp. 182–188.

C. Christiansen et al., "Prevention of Early Postmenopausal Bone Loss: Controlled 2–Year Study in 315 Normal Females," *Europ J Clin Invest,* 1980, 10, pp. 273–279.

J.M. Pouilles et al., "Prevention of Post–Menopausal Bone Loss with 1 α–Hydroxy Vitamin $D_3$, A Three–Year Prospective Study," *Clin Rheumatol.,* 11, 1992, 4, pp. 492–497.

M.F. Holick et al., *Proc. Natl. Acad. Sci. USA* 68, 803–804 (1971).

G. Jones et al., *Biochemistry* 14, 1250–1256 (1975).

M.F. Holick et al., *Science* 180, 190, 191 (1973).

H.Y. Lam et al., *Science* 486, 1038–1040 (1974).

S.M. Ott, C. H. Chestnut, *Annals of Int. Med.* 1989, 110:267–274.

(List continued on next page.)

*Primary Examiner*—Theodore J. Criares
*Attorney, Agent, or Firm*—Teresa J. Welch; Stroud, Stroud, Willink, Thompson & Howard

[57] ABSTRACT

The invention provides therapeutic methods for inhibiting, ameliorating or alleviating the hyperproliferative cellular activity of diseases of the prostate, e.g., prostatic cancer and prostatic hyperplasia, which includes administering to a patient in need thereof an active vitamin D analogue. Cell differentiation is promoted, induced or enhanced without causing to the patient dose-limiting hypercalcemia and hypercalciuria.

9 Claims, No Drawings

OTHER PUBLICATIONS

J.C. Gallagher et al., *Annals of Int. Med.* 1990, 113:649–655.

J. Aloia et al., *Amer. J. Med.* 84:401–08 (1988).

M. Shiraki et al., *Endocrinol. Japan* 32, 305–315 (1985).

G.F. Jensen et al., *Clin. Endocrinol.* 16, 515–524 (1982).

C. Christiansen et al., *Eur. J. Clin. Invest.* 11, 305–309 (1981).

O.H. Sorensen et al., *Clin. Endocrinol.* 7, 169S–175S (1977).

H. Orimo et al., *Bone and Mineral* 3, 47–52 (1987).

G. Sjoden et al., *J. Nutr.* 114, 2043–2046 (1984).

G. Sjoden et al., *Proc. Soc. Exp. Biol. Med.* 178, 432–436 (1985).

J.C. Gallagher et al., *Bone Min. Res.:* 1994; 9:607–614.

E. Braunwald et al., *Harrison's Principles of Internal Medicine:* Part Eleven, "Disorders of Bone and Mineral Metabolism," Chapter 335, McGraw–Hill, New York, 1987, pp. 1860–1865.

W. Grab, *Z. Physiol. Chem.*, 243:63–89 (1936).

F.G. McDonald, *J. Biol. Chem.*, 114:IVX (1936).

A. Windaus et al., *Z. Physiol. Chem.*, 247:185–188 (1937).

DeLuca et al., *Arch. Biochem, Biophys.*, 124:122–128 (1968).

*Merck Index*, S. Budavari (ed.), 11th ed., Merck & Co., Rahway, N.J. (1989) pp. 1579, #9930.

Barton et al., *JCS Perkin I*, 1976, 821–826.

Paaren et al., *J. Org. Chem.*, 1980, 45:3253.

S. Weintroub et al., "Dichotomy in the Effects of 1,25 dihydroxy vitamin $D_3$ and 24,25 dihydroxy vitamin $D_3$ on Bone Gamma–Carboxyglutamic Acid–Containing Protein in Serum and Bone in vitamin D–Deficient Rats," *Calcif, Tissue Int.* (1987) 40:166–172.

Strugnell et al., *Biochem. Pharm.* vol. 40:333–341 (1990).

Martin and DeLuca, *Am. J. Physiol.* 216:1352–1359 (1979).

P.J. Kocienski et al., *J.C.S. Perkins I*, 1290–1293 (1979).

M. Tsuji et al., *Bull. Chem. Soc. Jpn.*, vol. 63, No. 8, 2233–2238 (1990).

D.R. Crump et al., *J.C.S. Perkins Trans. I*, 2731–2733 (1973).

Chemical Abstracts, vol. 113, No. 1, 2 Jul. 1990, Columbus, Ohio, US; abstract No. 6683y, Y. Tachibana, 'Preparation of 1beta–hydroxyvitamin $D_2$ and $D_3$, ' p. 6688; col. 2; *abstract* & JP–A–02 011 563 (Nisshin Flour Miling Co.).

Chemistry Letters, No. 8, Aug. 1985, Tokyo, JP; pp. 1131–1132, H. Nemeto et al., 'A stereoselective synthesis of 1 alpha–hydroxy–vitamin $D_3$ ': *the whole document*.

F. Sato et al., *Biochim. Biophys. Acta*, vol. 1091 (1991) pp. 188–192.

METHOD OF TREATING PROSTATIC DISEASES USING ACTIVE VITAMIN D ANALOGUES

CROSS-REFERENCE TO RELATED APPLICATIONS

This application is a continuation-in-part of Ser. No. 08/415,488, Apr. 3, 1995, now U.S. Pat. No. 5,602,116 which is a continuation-in-part of Ser. No. 08/119,895, Sep. 10, 1993, now U.S. Pat. No. 5,403,831, and is also a continuation-in-part of Ser. No. 08/486,387, Jun. 7, 1995, now U.S. Pat. No. 5,674,859, which is a continuation-in-part of Ser. No. 08/265,438, Jun. 24, 1994, all of which are incorporated herein by reference.

STATEMENT REGARDING FEDERALLY SPONSORED RESEARCH OR DEVELOPMENT

Not Applicable

BACKGROUND OF THE INVENTION

This invention relates generally to a method of treating hyperproliferative prostatic diseases, and in particular, to the use of active forms of vitamin D to inhibit the hyperproliferative cellular activity of these diseases and to promote differentiation of the cells.

The prostate gland is found exclusively in male mammals and is subject to certain hyperproliferative diseases. A proliferation of basal and stroma cells of the prostate gland gives rise to benign prostatic hyperplasia which is one common prostate disease. Another common prostate disease is prostate cancer, especially prostatic adenocarcinoma. Adenocarcinoma of the prostate is common of the fatal pathophysiological prostate cancers, and typically involves a malignant transformation of epithelial cells in the peripheral region of the prostate gland. Both prostatic hyperplasia and prostate cancer have a high rate of incidence in the aging human male population. Approximately one out of every four males above the age of 55 suffers from a prostate disease of some form or another.

Prostate cancer is currently the second most frequent cause of cancer death after lung cancer among American males. Mortality rates for prostate cancer increase logarithmically with age and are two times higher in U.S. blacks than whites. Internationally, mortality rates are highest in U.S. blacks and in northern Europe and are lowest in Japan. It is projected that by the year 2000, a 90% increase in annual incidence of the disease and a 37% increase in annual mortality rates will be observed. Although prostate cancer may be a relatively indolent neoplasm in the elderly, the overall decrease in life span in patients with this disease is approximately 10 years.

Improvement in the treatment of prostate cancer has centered on early detection. In recent years, screening tests which detect certain proteins or peptides secreted by the prostate gland, i.e., markers, (e.g. prostate-specific antigen (PSA), prostatic acid phosphatase (PAP), prostatic inhibin (PIP)), have increased the power to diagnose this disease in asymptomatic patients.

Treatment of prostate cancer in men under the age of 65 has focused on radical surgery, e.g., prostatectomy, and/or radiotherapy, but the impact of these aggressive approaches on overall survival remains debatable. The approach to treatment of men over the age of 65 historically has been more conservative, and is based on the ablation or control of testosterone production. Such ablation or control is usually achieved by surgical castration, by administration of pituitary gonadotropin inhibitors such as estrogens or luteinizing hormone releasing hormone (LHRH) analogues, or a combination of these treatment methods. Estrogens, such as diethylstilbestrol, are potent inhibitors of the release from the pituitary gland of luteinizing hormone (LH), the gonadotropin that regulates testosterone production, and consequently, estrogen administration can cause a fall in testosterone to castration levels. Maximum suppression of plasma testosterone is typically achieved by a dosage of 3 mg/day of diethylstilbestrol. Other estrogens such as conjugated estrogens are about as equally effective in the lowering of the plasma level as diethylstilbestrol. However, diethylstilbestrol has a poor cardiovascular profile, and death from cardiovascular disease is not uncommon in patients treated with large doses of diethylstilbestrol. Thus, while dosages of up to 3 mg/day of diethylstilbestrol are typically safe, this treatment regime is not indicated for men with preexisting cardiovascular disease.

Prostatic carcinoma often metastasizes to the pelvis and lumbar vertebrae, causing bone loss and associated pain. Hormone manipulation often may result in significant palliation of metastatic prostate cancer, with improvement of bone pain and other disease-associated symptoms. Androgen ablation is, thus, also a major adjunctive therapy in advanced metastatic prostate cancer.

Despite initial improvement on hormonal treatment, a majority of patients with locally unresectable or metastatic disease will eventually fail to respond to further hormonal therapies. A recent study suggests that human prostate cancer cells may cycle between being androgen-independent and androgen-dependent. Such cycling may account for the return of the cancer after initial improvement. In this large group of patients, other forms of treatment, unfortunately, are far less effective. Radiotherapy often may relieve the symptoms of bone pain, but is not curative. Over time, the disease will progress with a fatal outcome.

As noted hereinabove, prostatic hyperplasia is another common hyperproliferative disease of the prostate gland. The disorder affects men over the age of 45 and increases in frequency with age. Prostatic hyperplasia begins in the periurethral region as a localized proliferation and progresses to compress the remaining normal gland. The hyperplasia can compress and obstruct the urethra. Treatment includes surgery, and administration of pituitary gonadotropin inhibitors and/or 5α-reductase enzyme inhibitors.

In another area of physiology and biochemistry, the vitamin D area, extensive research during the past two decades has established important biologic roles for vitamin D apart from its classic role in bone and mineral metabolism. Specific nuclear receptors for 1α,25-dihydroxyvitamin $D_3$, the hormonally active form of vitamin D, are present in cells from diverse organs not involved in calcium homeostasis. For example, Miller et al., 52 *Cancer Res.* (1992) 515–520, have demonstrated specific, biologically active receptors for 1α,25-dihydroxyvitamin $D_3$ in the human prostatic carcinoma cell line, LNCaP.

It has been reported that certain vitamin D compounds and analogues are potent inhibitors of malignant cell proliferation and are inducers/stimulators of cell differentiation. For example, U.S. Pat. No. 4,391,802 issued to Suda et al. discloses that 1α-hydroxyvitamin D compounds, specifically 1α,25-dihydroxyvitamin $D_3$ and 1α-hydroxyvitamin $D_3$, possess potent antileukemic activity by virtue of inducing the differentiation of malignant cells (specifically leukemia cells) to nonmalignant macrophages (monocytes), and are useful in the treatment of leukemia. Antiproliferative and differentiating actions of $1\alpha,25$-dihydroxyvitamin $D_3$ and other vitamin $D_3$ analogues have been reported with respect to prostate cancer cell lines. More recently, an association between vitamin D receptor gene polymorphism and prostate cancer risk has been reported, suggesting that vitamin D receptors may have a role in the development, and possible treatment, of prostate cancer.

These previous studies have focused exclusively on vitamin $D_3$ compounds. Even though these compounds may indeed be highly effective in promoting differentiation in malignant cells in culture, their practical use in differentiation therapy as anticancer agents is severely limited because of their equally high potency as agents affecting calcium metabolism. At the levels required in vivo for effective use as, for example, antileukemic agents, these same compounds can induce markedly elevated and potentially dangerous blood calcium levels by virtue of their inherent calcemic activity. That is, the clinical use of $1\alpha,25$-dihydroxyvitamin $D_3$ and other vitamin $D_3$ analogues as anticancer agents is precluded, or severely limited, by the risk of hypercalcemia. This indicates a need for compounds with greater specific activity and selectivity of action, i.e., vitamin D compounds with antiproliferative and differentiating effects but which have less calcemic activity. The need for such compounds is no greater than in the treatment of neoplastic and hyperplastic prostatic diseases.

BRIEF SUMMARY OF THE INVENTION

The present invention provides a method of treating prostatic disease conditions such as those characterized by hyperproliferative cell growth and/or abnormal cell differentiation, e.g., prostate cancer and prostatic hyperplasia. The method includes use of active vitamin D compounds to inhibit abnormal cell growth and promote cell differentiation.

The foregoing, and other advantages of the present invention, are realized in one aspect thereof in a method of inhibiting the hyperproliferative activity of human neoplastic or hyperplastic cells, comprising treating the cells with an effective amount of a $1\alpha$-hydroxyvitamin D compound having a hydrocarbon moiety substituted at the C-24 position on the sidechain of the molecule. The treating step includes inhibiting proliferation of, and inducing and enhancing differentiation in such prostatic cells.

The $1\alpha$-hydroxyvitamin D compound is an active vitamin D and is suitably represented by the formula (I) described hereinafter. Preferred among the compounds of formula (I), are $1\alpha,24$-dihydroxyvitamin $D_2$, $1\alpha,24$-dihydroxyvitamin $D_4$, $1\alpha,25$-dihydroxyvitamin $D_4$, $1\alpha,25$-dihydroxyvitamin $D_2$, $1\alpha$-hydroxyvitamin $D_2$ and $1\alpha$-hydroxyvitamin $D_4$.

The effective or therapeutic amount of the $1\alpha$-hydroxyvitamin D compound administrable in accordance with the present invention to patients in need on a daily basis per kilogram of body weight ranges from 0.01 µg/kg/day to 2.0 µg/kg/day.

In another aspect, the invention is a method of treating human prostate cancer, comprising administering to a male subject who has prostate cancer an effective amount of an active vitamin D compound which has, or attains through metabolism in vivo, a vitamin D receptor (VDR) binding affinity substantially equivalent to the binding affinity of $1\alpha,25$-dihydroxyvitamin $D_3$ and a hypercalcemia risk substantially lower than that of $1\alpha,25$-dihydroxyvitamin $D_3$, to decrease or stabilize the cellular abnormal proliferative activity of the cancer.

For treatment for prostate conditions in accordance with the present invention, the active vitamin D is suitably administered alone as an active ingredient, i.e., as a first anticancer agent, in a pharmaceutical composition, or in a mixture including a second anticancer agent, an androgen abalation agent, a $5\alpha$-reductase inhibitor or combinations thereof.

In another aspect, the invention is a pharmaceutical composition which includes a first anticancer agent which is an active vitamin D compound; an agent selected from the group consisting of (i) a second anticancer agent, (ii) a bone agent, (iii) an androgen ablation agent and (iv) a $5\alpha$-reductase inhibitor and combinations thereof; and a physiologically acceptable carrier.

Other advantages and a fuller appreciation of specific adaptations, compositional variations, and physical attributes will be gained upon an examination of the following detailed description of preferred embodiments, taken in conjunction with the appended claims.

BRIEF DESCRIPTION OF THE DRAWING(S)

Not Applicable

DETAILED DESCRIPTION OF THE INVENTION

The present invention provides an effective method for the treatment of neoplastic and hyperplastic diseases. Particularly, the present invention relates to therapeutic methods for inhibiting, ameliorating or alleviating the hyperproliferative cellular activity of diseases of the prostate, e.g., prostatic cancer and prostatic hyperplasia, and inducing, enhancing or promoting cell differentiation in the diseased cells. The present invention provides a novel treatment of a patient suffering from a hyperproliferative disease such as prostatic cancer or prostatic hyperplasia with an active vitamin D analogue having a hydrocarbon moiety substituted at the C-24 position of the sidechain of the molecule. Preferably, the active vitamin D analogue is a $1\alpha$-hydroxyvitamin D compound and is suitably represented by formula (I) as described hereinbelow. The active vitamin D analogue is provided to the patient without causing dose-limiting hypercalcemia and hypercalciuria, i.e., unphysiologically high and deleterious blood calcium levels and urine calcium levels, respectively. These attributes are achieved through specific chemical properties of the compounds of formula (I) described.

In accordance with the present invention, when effective amounts of the analogues of formula (I) are administered to patients with prostatic cancer or prostatic hyperplasia, the proliferative activity of the abnormal prostatic cells is inhibited or alleviated, and cell differentiation is induced, promoted or enhanced, with significantly less hypercalcemia and hypercalciuria than is observed after the same amount of activated vitamin $D_3$ is administered in previously known formulations. Thus, the compounds of formula (I) have an improved therapeutic index relative to active forms of vitamin $D_3$ analogues.

It is known that vitamin $D_3$ must be hydroxylated in the C-1 and C-25 positions before it is activated, i.e., before it will produce a biological response. A similar metabolism appears to be required to activate other forms of vitamin D, e.g., vitamin $D_2$ and vitamin $D_4$. Therefore, as used herein, the term "activated vitamin D" or "active vitamin D" is intended to refer to a vitamin D compound or analogue that has been hydroxylated in at least the C-1 position of the A ring of the molecule and either the compound itself or its metabolites in the case of a prodrug, such as 1α-hydroxyvitamin D₂, binds the vitamin D receptor (VDR). Vitamin D compounds which are hydroxylated only in the C-1 position are referred to herein as "prodrugs." Such compounds undergo further hydroxylation in vivo and their metabolites bind the VDR.

Also, as used herein, the term "lower" as a modifier for alkyl, alkenyl acyl, or cycloalkyl is meant to refer to a straight or branched, saturated or unsaturated hydrocarbon radical having 1 to 4 carbon atoms. Specific examples of such hydrocarbon radicals are methyl, ethyl, propyl, isopropyl, butyl, isobutyl, t-butyl, ethenyl, propenyl, butenyl, isobutenyl, isopropenyl, formyl, acetyl, propionyl, butyryl or cyclopropyl. The term "aromatic acyl" is meant to refer to a unsubstituted or substituted benzoyl group.

As used herein, the term "hydrocarbon moiety" refers to a lower alkyl, a lower alkenyl, a lower acyl group or a lower cycloalkyl, i.e., a straight or branched, saturated or unsaturated $C_1$–$C_4$ hydrocarbon radial.

The compound in accordance with the present invention is an active vitamin D compound provided that such compound has a hydrocarbon moiety at the C-24 position, e.g., a lower alkyl, alkenyl or acyl group at the C-24 position. Further, the active vitamin D in accordance with the present invention may have an unsaturated sidechain, e.g., there is suitably a double bond between C-22 and C-23, between C-25 and C-26 or between C-26 and C-27.

The 1α-hydroxyvitamin D of the present invention preferably has the general formula described in formula (I)

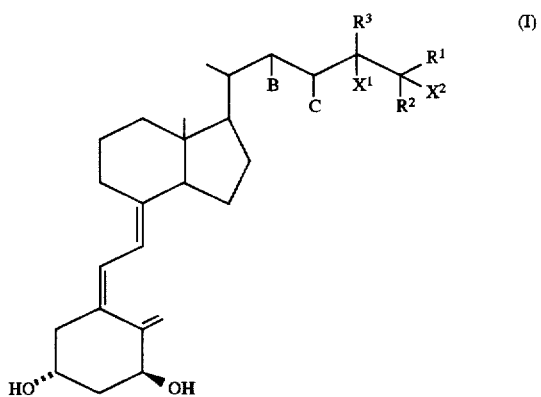

wherein B and C each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, and $X^2$ is hydrogen or hydroxyl, or, may be taken with $R^1$ or $R^2$, to constitute a double bond.

The 1α-hydroxyvitamin D compounds of formula (I) of the present invention are those that have effective antiproliferative and cell differentiation activity (i.e., reversal of malignant transformation), particularly with respect to cells of prostatic diseases, e.g., prostatic cancer and prostatic hyperplasia, but have a lower tendency or inability to cause the undesired side effects of hypercalcemia and/or hypercalciuria. In other words, the compounds of formula (I) can be administered at dosages that allow them to act as antiproliferative agents and cell differentiation agents when exposed to malignant or other hyperproliferative cells without significantly altering calcium metabolism. This selectivity and specificity of action makes the 1α-hydroxyvitamin D compounds of formula (I) useful and preferred agents for safely inhibiting hyperproliferation and promoting malignant or hyperplastic cell differentiation. The 1α-hydroxyvitamin D compounds of the present invention, thus, overcome the shortcomings of the known active vitamin $D_3$ compounds described above, and can be considered preferred agents for the control and treatment of malignant diseases such as prostate cancer as well as benign prostatic hyperplasia.

Preferred among the active vitamin D compounds of formula (I) are: 1α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$, and 1α-hydroxyvitamin $D_4$. Among those compounds of formula (I) that have a chiral center in the sidechain, such as at C-24, it is understood that both epimers (e.g., R and S) and the racemic mixture are within the scope of the present invention.

Thus, the present invention provides a method of treating malignant prostatic cells as well as other hyperproliferative prostatic cells, (i.e., inhibiting their hyperproliferative activity and/or inducing and enhancing their differentiation) with an effective amount of a compound of formula (I). The effective dosage amount on a daily basis per kilogram of body weight of the patient ranges from about 0.01 µg/kg/day to about 2.0 µg/kg/day.

The compounds of formula (I) are valuable for the treatment of prostate cancer and prostatic hyperplasia in a patient suffering therefrom. In particular, the invention is a method for treating a patient suffering from the hyperproliferative cellular effects of prostate cancer and prostatic hyperplasia by administering to the patient a therapeutically effective amount of a compound of formula (I), which is preferably 1,α,24-dihydroxyvitamin $D_2$, 1α,24-dihydroxyvitamin $D_4$, 1α,25-dihydroxyvitamin $D_2$, 1α,25-dihydroxyvitamin $D_4$, 1α-hydroxyvitamin $D_2$, and 1α-hydroxyvitamin $D_4$.

The compounds of formula (I) can be prepared as described, e.g., in U.S. Pat. No. 5,448,120 issued to Knutson et al., U.S. Pat. No. 4,554,106 issued to DeLuca et al., and Strugnell et al., 310 *Biochem. J.* (1995) pp. 233–241, all of which are incorporated herein by reference.

The biopotencies of the compounds of formula (I) have been studied and compared to that of 1α,25-dihydroxyvitamin $D_3$, the active hormonal form of vitamin D and the standard against which all vitamin D compounds and analogues are measured. For example, it has been found that the vitamin D receptor (VDR) binding affinities of the compounds of formula (I), or their active metabolites, are substantially equivalent to (i.e., equal to or up to 3 times weaker than) the affinity of 1α,25-dihydroxyvitamin $D_3$. Such receptor binding affinities are indicative of potent biological activity.

At the same time, it has been found that compounds of formula (I) are significantly less toxic than their corresponding vitamin $D_3$ analogues. For example, in parent co-pending application, Ser. No. 08/265,438, the disclosure of which is incorporated herein by reference, the $LD_{50}$ for 1α-hydroxyvitamin $D_4$ was found to be 1.0 mg/kg in males and 3.0 mg/kg in females, i.e., substantially less toxic than 1α-hydroxyvitamin $D_3$ ($LD_{50}$0.2 mg/kg). Further, in the parent U.S. Pat. No. 5,403,831, and its grandparent U.S. Pat. No. 5,104,864, both of which are incorporated herein by reference, it has been shown that 1α-hydroxyvitamin $D_2$ has the same biopotency as 1α-hydroxyvitamin $D_3$ and 1α,25-dihydroxyvitamin $D_3$ but is much less toxic. Even dosages up to 10 µg/day of 1α-hydroxyvitamin $D_2$ in women with postmenopausal osteoporosis elicited only mild hypercalciuria (U.Ca >300 mg/24 hrs), and no marked hypercalcemia (S. Ca>11.0 mg/dL) solely due to 1α-hydroxyvitamin $D_2$ was evident. Additionally, the compound did not adversely affect kidney function, as determined by creatinine clearance and BUN; nor did it increase urinary excretion of hydroxyproline, indicating the absence of any stimulatory effect on bone resorption. Administration of 1α-hydroxyvitamin $D_2$ to healthy adult males in dosages up to 8 µg/day showed no clinically significant hypercalcemia or other adverse effects.

The compounds of formula (I) are useful as active compounds in pharmaceutical compositions having reduced side effects and low toxicity as compared with the known analogues of active forms of vitamin $D_3$.

The pharmacologically active compounds of this invention can be processed in accordance with conventional methods of pharmacy to produce medicinal agents for administration to patients, e.g., mammals including humans. For example, the compounds of formula (I) can be employed in admixtures with conventional excipients, e.g., pharmaceutically acceptable carrier substances suitable for enteral (e.g., oral) or parenteral application which do not deleteriously react with the active compounds.

Suitable pharmaceutically acceptable carriers include but are not limited to water, salt solutions, alcohols, gum arabic, vegetable oils (e.g., corn oil, cottonseed oil, peanut oil, olive oil, coconut oil), fish liver oils, oily esters such as Polysorbate 80, polyethylene glycols, gelatin, carbohydrates (e.g., lactose, amylose or starch), magnesium stearate, talc, silicic acid, viscous paraffin, fatty acid monoglycerides and diglycerides, pentaerythritol fatty acid esters, hydroxy methylcellulose, polyvinyl pyrrolidone, etc.

The pharmaceutical preparations can be sterilized and, if desired, be mixed with auxiliary agents, e.g., lubricants, preservatives, stabilizers, wetting agents, emulsifiers, salts for influencing osmotic pressure, buffers, coloring, flavoring and/or one or more other active agents.

For parenteral application, particularly suitable are injectable, sterile solutions, preferably oily or aqueous solution, as well as suspensions, emulsions, or implants, including suppositories. Ampules are convenient unit dosages.

For enteral application, particularly suitable are tablets, dragees, liquids, drops, lozenges, powders, or capsules. A syrup, elixir, or the like can be used if a sweetened vehicle is desired.

For rectal administration, compounds are formed into a pharmaceutical composition containing a suppository base such as cacao oil or other triglycerides. To prolong storage life, the composition advantageously includes an antioxidant such as ascorbic acid, butylated hydroxyanisole or hydroquinone.

Oral administration of the pharmaceutical compositions of the present invention is preferred. The dosage of the compounds for the treatment of prostatic cancer or hyperplasia according to this invention generally is about 0.01 to about 2.0 µg/kg/day, preferably about 0.01 to about 1.0 µg/kg/day. Generally, the compounds of this invention are dispensed by unit dosage form in a pharmaceutically acceptable carrier.

For treatment of prostate cancer, the parenteral dosage of the compounds of formula (I) is about 0.01 µg/kg/day to about 1.0 µg/kg/day.

It will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, body weight, general state of health, on diet, on the timing and mode of administration, on the rate of excretion, and on medicaments used in combination and the severity of the particular disorder to which the therapy is applied. Dosages for a given host can be determined using conventional considerations, e.g., by customary comparison of the differential activities of the subject compounds and of a known agent, such as by means of an appropriate conventional pharmacological protocol.

Also included within the scope of the present invention is the co-administration of a compound of formula (I) with known androgen control or ablation or testosterone level-lowering agents such as estrogens (e.g., diethylstilbestrol), LHRH analogues, 5α-reductase enzyme inhibitors such as finasteride, antiestrogens (e.g., Tamoxifen™), and antiandrogens (e.g., flutamide). (See, e.g., U.S. Pat. No. 5,372,996, incorporated herein by reference.) It is anticipated that a symbiotic effect is obtainable with these various combinations, and will provide an increased therapeutic effect. Also, there is the potential to provide therapy wherein the adverse side effects with some of these agents, e.g., the deleterious cardiovascular effects of estrogens, are considerably reduced compared to when these agents are used alone in larger dosages. Possible dose ranges of these co-administered androgen control or testosterone level-lowering agents are about 0.01 to 0.20 µg/kg/day.

Further, included within the scope of the present invention is the co-administration of the active vitamin D of formula (I) with a second anticancer agent, e.g., a cytotoxic agent, particularly in metastatic prostate cancer wherein relapse has occurred following hormonal treatment. Such agents may suitably include estramustine phosphate, prednimustine, cisplatin, 5-fluoro-uracil, melphalan, hydroxyurea, mitomycin, idarubicin, methotrexate, adriamycin and daunomycin. It is anticipated that an active vitamin D of formula (I) used in combination with various anticancer drugs can give rise to a significantly enhanced cytotoxic effect on cancerous cells, thus providing an increased therapeutic effect. Specifically, as a significantly increased growth-inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the anticancer drugs used alone in larger doses. Possible dose ranges of these co-administered second anticancer agents are about 0.1 to 1 µg/kg/day.

Also included within the scope of the present invention is the co-administration of effective dosages of the analogue of formula (I) in conjunction with administration of hormones or other agents, e.g., estrogens, which are known to ameliorate bone diseases or disorders. As noted above, prostate cancer often metastasizes to bone, causing bone loss and associated pain. Such bone agents may include conjugated estrogens or their equivalents, calcitonin, bisphosphonates, calcium supplements, cobalamin, pertussis toxin and boron. Possible dose ranges for these co-administered bone agents are provided in Table 1.

TABLE 1

Possible Oral Dose Ranges for Various Bone Agents
Co-Administered With 1α-Hydroxyvitamin D of Formula (I)

| Agent | Dose Ranges | | |
|---|---|---|---|
| | Broad | Preferred | Most Preferred |
| Conjugated Estrogens or Equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Bisphosphonates (mg/day) | 0.5–20 | 1–15 | 5–10 |
| Calcium Supplements (mg/day) | 250–2500 | 500–1500 | 750–1000 |
| Cobalamin (μg/day) | 5–200 | 20–100 | 30–50 |
| Pertussis Toxin (mg/day) | 0.1–2000 | 10–1500 | 100–1000 |
| Boron (mg/day) | 0.10–3000 | 1–250 | 2–100 |

Antiestrogens, such as Tamoxifen™, are also known bone agents and may be suitably used in conjunction with the 1α-hydroxyvitamin D compounds of the present invention.

The present invention is further explained by the following examples which should not be construed by way of limiting the scope of the present invention.

VDR BINDING ANALYSES

Example 1: 1α,24-dihydroxyvitamin $D_2$ [1α,24-$(OH)_2D_2$]

The affinity of 1α,24-$(OH)_2D_2$ for the mammalian vitamin D receptor (VDR) was assessed using a commercially available kit of bovine thymus VDR and standard 1,25-$(OH)_2D_3$ solutions from Incstar (Stillwater, Minn.). The half-maximal binding of chemically synthesized 1α,24-$(OH)_2D_2$ was approximately 150 pg/ml whereas that of 1α,25-$(OH)_2D_3$ was 80 pg/ml. Thus, the 1α,24-$(OH)_2D_2$ had a very similar affinity for bovine thymus VDR as did 1α,25-$(OH)_2D_3$, indicating that 1α,24-$(OH)_2D_2$ has potent biological activity.

Example 2: 1α,24-dihydroxy vitamin $D_4$ [1α,24-$(OH)_2D_4$]

The VDR affinity binding of 1α,24-$(OH)_2D_4$ was investigated. The 1α,24-$(OH)_2D_4$ was incubated with vitamin D receptor and radiolabeled tracer 1α,25-$(OH)_2D_3$. After incubation, the amount of radioactivity bound to the receptor was determined and compared with the amount bound after co-incubation of unlabeled and labeled 1α,25-$(OH)_2D_3$. It was found that 50 pg/tube of 1α,24-$(OH)_2D_4$ was equivalent to approximately 20 pg 1α,25-$(OH)_2D_3$.

These results show that 1α,24-$(OH)_2D_4$ binds slightly less tightly to the vitamin D receptor than does 1α,25-$(OH)_2D_3$. Such data mean that 1α,24-$(OH)_2D_4$ has high affinity for the VDR and significant biological activity, similar to that of 1α,25-$(OH)_2D_3$. These data are consistent with gene expression studies done (described below) with 1α,24-$(OH)_2D_4$ which demonstrate that 1α,24-$(OH)_2D_4$ is only slightly less active than is 1α,25-$(OH)_2D_3$.

These results are surprising and unexpected in view of the prior art. They are contrary to the normative wisdom in the vitamin D art regarding the very low degree of biological activity of vitamin $D_4$ compounds.

Example 3: 1α,24-dihydroxyvitamin $D_2$ [1α,24-$(OH)_2D_2$]

VDR binding of vitamin D compounds by prostate cells is demonstrated using the techniques of Skowronski et al., 136 *Endocrinology* (1995) 20–26, which is incorporated herein by reference. Prostate-derived cell lines are cultured to near confluence, washed and harvested by scraping. Cells are washed by centrifugation, and the cell pellet resuspended in a buffered salt solution containing protease inhibitors. The cells are disrupted by sonication while cooling on ice. The supernatant obtained from centrifuging the disrupted cells at 207,000×g for 35 min at 4° C. is assayed for binding. 200 μL of soluble extract, (1–2 mg protein/ml supernatant) is incubated with a 1 nM $^3$H-1α,25-$(OH)_2D_3$ and increasing concentrations of 1α,24-$(OH)_2$-$D_2$ (0.01–100 nM) for 16–20 hr at 4° C. Bound and free hormones are separated with hydroxylapatite using standard procedures. Specific binding is calculated by subtracting nonspecific binding obtained in the presence of a 250-fold excess of nonradioactive 1α,25-$(OH)_2D_3$ from the total binding measured. The results demonstrate that 1α,24-$(OH)_2D_2$ has strong affinity for prostate VDR, indicating that 1α,24-$(OH)_2D_2$ has potent biological activity in respect of prostate cells.

Example 4: 1α,24-dihydroxy vitamin $D_4$ [1α,24-$(OH)_2D_4$]

The procedure of Example 3 is repeated using the active vitamin D analogue 1α,24-$(OH)_2D_4$, and the specific binding is determined. The results demonstrate that 1α,24-$(OH)_2D_4$ has strong affinity for prostate VDR, indicating that 1α,24-$(OH)_2D_4$ has potent biological activity in respect of prostate cells.

Example 5: 1α,25-dihydroxyvitamin $D_4$ [1α,25-$(OH)_2D_4$]

The procedure of Example 3 is repeated using the active vitamin D analogue 1α,25-$(OH)_2D_4$, and the specific binding is determined. The results demonstrate that 1α,25-$(OH)_2D_4$ has strong affinity for prostate VDR, indicating that 1α,25-$(OH)_2D_4$ has potent biological activity in respect of prostate cells.

GENE EXPRESSION

Example 6: 1α,24-dihydroxy vitamin $D_4$ [1α,24-$(OH)_2D_4$]

Using the plasmids p(CT4)$^4$TKGH, a vitamin D receptor (VDR)-expressing plasmid, and pSG5-hVDR1/3, a plasmid containing a Growth Hormone (GH) gene, under the control of a vitamin D-responsive element (VDRE), experiments were conducted to explore the ability of 1α,24-$(OH)_2D_4$ to induce vitamin D-dependent growth hormone acting as a reporter gene compared to that of 1α,25-$(OH)_2D_3$. Cells in culture were transfected with these two plasmids. One plasmid contained the gene for Growth Hormone (GH) under the control of the vitamin D responsive element (VDRE) and the other plasmid contained the structural gene for the vitamin D receptor (VDR). These transfected cultures were incubated with 1α,24-$(OH)_2D_4$ or 1α,25-$(OH)_2D_3$, and the production of growth hormone was measured. Table 2 below shows the results of this assay:

TABLE 2

Induction of Growth Hormone by Vitamin D Compounds

| Compound | Concentration Used (M) | Growth Hormone Induction (ng/ml) |
|---|---|---|
| 1,25-$(OH)_2D_3$ | $1 \times 10^{-10}$ | 39 |
| 1,25-$(OH)_2D_3$ | $5 \times 10^{-10}$ | 248 |
| 1,24-$(OH)_2D_4$ | $5 \times 10^{-10}$ | 165 |

TABLE 2-continued

Induction of Growth Hormone by Vitamin D Compounds

| Compound | Concentration Used (M) | Growth Hormone Induction (ng/ml) |
|---|---|---|
| 1,24-(OH)$_2$D$_4$ | 1 × 10$^{-9}$ | 628 |
| 1,24-(OH)$_2$D$_4$ | 5 × 10$^{-9}$ | 1098 |

These data show that the ability of 1α,24-(OH)$_2$D$_4$ to stimulate vitamin D-dependent growth hormone is nearly equivalent to that of 1α,25-(OH)$_2$D$_3$. Such results are truly surprising and would not have been expected by following the teachings of the prior art.

Example 7: 1α,24(S)-dihydroxyvitamin D$_2$ and 1α, 24(R)-dihydroxyvitamin D$_2$ [1α,24(S)-(OH)$_2$D$_2$ and 1α,24(R)-(OH)$_2$D$_2$]

The gene expression study described in Example 6 was conducted to compare the biological activity in vitro of chemically synthesized 1α,24(S)-(OH)$_2$D$_2$ and 1α,24(R)-(OH)$_2$D$_2$, with 1α,25-(OH)$_2$D$_3$ and 25-OH-D$_3$. The vitamin D-dependent transcriptional activation model system was used in which plasmids pSG5-hVDR1/3 and p(CT4)$^4$TKGH were co-transfected into Green monkey kidney, COS-1 cells.

Transfected cells were incubated with vitamin D metabolites and growth hormone production was measured. As shown in Table 3, both 1α,24(S)-(OH)$_2$D$_2$ and its epimer, 1α,24(R)-(OH)$_2$D$_2$, had significantly more activity in this system than 25-OH-D$_3$, with 1α,24(S)-(OH)$_2$D$_2$ having nearly the same activity as 1α,25-(OH)$_2$D$_3$.

TABLE 3

Vitamin D-Inducible Growth Hormone Production In Transfected COS-1 Cells

| Inducer | Molar Concentration | Total GH Production* (ng/ml) | Net vitamin D-inducible GH-production (ng/ml) |
|---|---|---|---|
| Ethanol | | 44 | 0 |
| 25-OH-D$_3$ | 1 × 10$^{-7}$ | 245 | 201 |
| | 1 × 10$^{-6}$ | 1100 | 1056 |
| | 1 × 10$^{-5}$ | 775 | 731 |
| 1α,25-(OH)$_2$D$_3$ | 1 × 10$^{-10}$ | 74 | 30 |
| | 1 × 10$^{-9}$ | 925 | 881 |
| | 1 × 10$^{-8}$ | 1475 | 1441 |
| 1α,24(S)-(OH)$_2$D$_2$ | 5 × 10$^{-10}$ | 425 | 381 |
| | 5 × 10$^{-9}$ | 1350 | 1306 |
| | 5 × 10$^{-8}$ | 1182 | 1138 |
| 1α,24(R)-(OH)$_2$D$_2$ | 1 × 10$^{-9}$ | 80 | 36 |
| | 1 × 10$^{-8}$ | 1100 | 1056 |
| | 1 × 10$^{-7}$ | 1300 | 1256 |

*Averages of duplicate determinations

INHIBITION OF PROSTATE CELL PROLIFERATION

Example 8: 1α,24-dihydroxyvitamin D$_2$ [1α,24-(OH)$_2$D$_2$]

Inhibition of cell proliferation is demonstrated using the techniques of Skowronski et al., 132 *Endocrinology* (1993) 1952–1960 and 136 *Endocrinology* (1995) 20–26, both of which are incorporated herein by reference. The cell lines, LNCaP and PC-3, which are derived from human prostate adenocarcinoma, are seeded in six-well tissue culture plates at a density of about 50,000 cells/plate. After the cells have attached and stabilized, about 2–3 days, the medium is replenished with medium containing vehicle or the active vitamin D analogue 1α,24-(OH)$_2$D$_2$, at concentrations from 10$^{-11}$ M to 10$^{-7}$ M. Medium containing test analogue or vehicle is replaced every three days. After 6–7 days, the medium is removed, the cells are rinsed, precipitated with cold 5% trichloroacetic acid, and washed with cold ethanol. The cells are solubilized with 0.2N sodium hydroxide, and the amount of DNA determined by standard procedures. The results show that cultures incubated with 1α,24-(OH)$_2$D$_2$ in accordance with the present invention have significantly fewer cells than the control cultures.

Example 9: 1α,24-dihydroxy vitamin D$_4$ [1α,24-(OH)$_2$D$_4$]

The procedure of Example 8 is repeated using the active vitamin D analogue 1α,24-(OH)$_2$D$_4$, and the cell number is determined. Cultures incubated with 1α,24-(OH)$_2$D$_4$ have significantly fewer cells than the control cultures.

Example 10: 1α,25-dihydroxyvitamin D$_4$ [1α,25-(OH)$_2$D$_4$]

The procedure of Example 8 is repeated using the active vitamin D analogue 1α,25-(OH)$_2$D$_4$, and the cell number is determined. Cultures incubated with 1α,25-(OH)$_2$D$_4$ have significantly fewer cells than the control cultures.

STIMULATION OF PROSTATE CELL DIFFERENTIATION

Example 11: 1α,24-dihydroxyvitamin D$_2$ [1α,24-(OH)$_2$D$_2$]

Using the techniques of Skowronski et al., 132 *Endocrinology* (1993) 1952–1960 and 136 *Endocrinology* (1995) 20–26, both of which are incorporated herein by reference, cells of the cell line, LNCaP, which is derived from a human metastatic prostate adenocarcinoma and known to express PSA, are seeded in six-well tissue culture plates at a density of about 50,000 cells/plate. After the cells have attached and stabilized, about 2–3 days, the medium is replenished with medium containing vehicle or the active vitamin D analogue, 1α,24-(OH)$_2$D$_2$, at concentrations from 10$^{-11}$M to 10$^{-7}$M. After 6–7 days, the medium is removed and stored at −20° C. for prostate specific antigen (PSA) analysis.

The cells from parallel cultures are rinsed, precipitated, and the amount of DNA determined by standard procedures. PSA is measured by standard known methods. Cultures incubated with 1α,24-(OH)$_2$D$_2$ have significantly more PSA than control cultures when expressed as mass of PSA/cell.

Example 12: 1α,24-dihydroxyvitamin D$_4$ [1α,24-(OH)$_2$D$_4$]

The procedure of Example 12 is repeated except the active vitamin D analogue is 1α,24-(OH)$_2$D$_4$. The PSA is measured and cultures incubated with 1α,24-(OH)$_2$D$_4$ have significantly more PSA than control cultures when expressed as mass of PSA/cell.

Example 13: 1α,25-dihydroxyvitamin D$_4$ [1α,24-(OH)$_2$D$_4$]

The procedure of Example 12 is repeated except the active vitamin D analogue is 1α,25-(OH)$_2$D$_4$. The PSA is measured and cultures incubated with 1α,25-(OH)$_2$D$_4$ have significantly more PSA than control cultures when expressed as mass of PSA/cell.

CLINICAL STUDIES

Example 14: 1α,24-dihydroxy vitamin D$_2$ [1α,24-(OH)$_2$D$_2$]

Patients with advanced androgen-independent prostate cancer participate in an open-labeled study of 1α,24-(OH)$_2$D$_2$. Qualified patients are at least 40 years old, exhibit histologic evidence of adenocarcinoma of the prostate, and present with progressive disease which had previously responded to hormonal intervention(s). On admission to the study, patients begin a course of therapy with oral 1α,24-(OH)$_2$D$_2$ lasting 26 weeks, while discontinuing any previous use of calcium supplements, vitamin D supplements, and vitamin D hormone replacement therapies. During treatment, the patients are monitored at regular intervals for: (1) hypercalcemia, hyperphosphatemia, hypercalciuria, hyperphosphaturia and other toxicity; (2) evidence of changes in the progression of metastatic disease; and (3) compliance with the prescribed test drug dosage.

The study is conducted in two phases. During the first phase, the maximal tolerated dosage (MTD) of daily oral 1α,24-(OH)$_2$D$_2$ is determined by administering progressively higher dosages to successive groups of patients. All doses are administered in the morning before breakfast. The first group of patients is treated with 25.0 μg of 1α,24-(OH)$_2$D$_2$. Subsequent groups of patients are treated with 50.0, 75.0 and 100.0 μg/day. Dosing is continued uninterrupted for the duration of the study unless serum calcium exceeds 11.6 mg/dL, or other toxicity of grade 3 or 4 is observed, in which case dosing is held in abeyance until resolution of the observed toxic effect(s) and then resumed at a level which has been decreased by 10.0 μg.

Results from the first phase of the study show that the MTD for 1α,24-(OH)$_2$D$_2$ is above 20.0 μg/day, a level which is 10- to 40-fold higher than can be achieved with 1α,25-(OH)$_2$D$_3$. Analysis of blood samples collected at regular intervals from the participating patients reveal that the levels of circulating 1α,24-(OH)$_2$D$_2$ increase proportionately with the dosage administered, rising to maximum levels well above 100 pg/mL at the highest dosages, and that circulating levels of 1α,25-(OH)$_2$D$_3$ are suppressed, often to undetectable levels. Serum and urine calcium are elevated in a dose responsive manner. Patients treated with the MTD of 1α,24-(OH)$_2$D$_2$ for at least six months report that bone pain associated with metastatic disease is significantly diminished.

During the second phase, patients are treated with 1α,24-(OH)$_2$D$_2$ for 24 months at 0.5 and 1.0 times the MTD. After one and two years of treatment, CAT scans, X-rays and bone scans used for evaluating the progression of metastatic disease show stable disease or partial remission in many patients treated at the lower dosage, and stable disease and partial or complete remission in many patients treated at the higher dosage.

Example 15: 1α-hydroxyvitamin D$_2$ [1α-OH-D$_2$]

The study of Example 14 is repeated for the active vitamin D compound, 1α-OH-D$_2$. The results of the phase one study indicate that patients treated with the MTD of 1α-OH-D$_2$ for at least six months report that bone pain associated with metastatic disease is significantly diminished. The results of the phase two study indicate that after two years, CAT scans, X-rays and bone scans used for evaluating the progression of metastatic disease show stable disease or partial remission in many patients treated at the lower dosage, and stable disease and partial or complete remission in many patients treated at the higher dosage.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation lawfully accorded the appended claims.

We claim:

1. A method of inhibiting the hyperproliferative activity of human prostatic neoplastic or hyperplastic cells, comprising treating the cells with an effective amount of a 1α-hydroxyvitamin D compound having a hydrocarbon moiety substituted at C-24.

2. The method of claim 1, wherein said 1α-hydroxvitamin D compound is represented by formula (I)

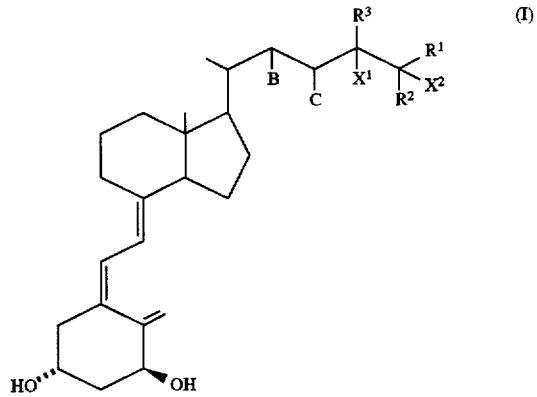

wherein B and C each are hydrogen or a carbon-carbon bond, thus forming a double bond between C-22 and C-23; R$^1$ and R$^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that R$^1$ and R$^2$ cannot both be an alkenyl group, or taken together with the carbon to which they are bonded, form a C$_3$–C$_8$, cyclocarbon ring; R$^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; X$^1$ is hydrogen or hydroxyl, or, taken with R$^3$, constitutes a bond when R$^3$ is an alkenyl group, and X$^2$ is hydrogen or hydroxyl, or, taken with R$^1$ or R$^2$, constitutes a double bond.

3. The method of claim 2, wherein the compound of formula (I) is 1α,24-dihydroxyvitamin D$_2$, 1α,24-dihydroxyvitamin D$_4$, 1α,25-dihydroxyvitamin D$_2$, 1α,25-dihydroxyvitamin D$_4$, 1α-hydroxyvitamin D$_2$ or 1α-hydroxyvitamin D$_4$.

4. The method of claim 1, wherein said treating step includes inhibiting proliferation of, and inducing and enhancing differentiation in said prostatic cells.

5. A method for the treatment of prostatic diseases characterized by abnormal cell differentiation or cell proliferation, comprising administering to a male human or animal in need of such treatment an effective proliferation-inhibiting amount of a compound of formula (I)

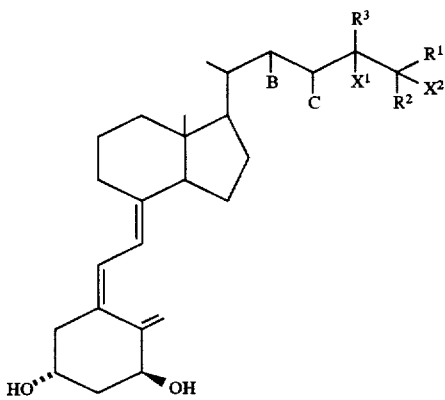

(I)

wherein B and C each are hydrogen or a carbon-carbon bond, thus forming a double bond between C-22 and C-23; $R^1$ and $R^2$ are identical or different and are hydrogen, hydroxyl, lower alkyl, lower fluoroalkyl, O-lower alkyl, lower alkenyl, lower fluoroalkenyl, O-lower alkenyl, O-lower acyl, O-aromatic acyl, lower cycloalkyl with the proviso that $R^1$ and $R^2$ cannot both be an alkenyl group, or taken together with the carbon to which they are bonded, form a $C_3$–$C_8$ cyclocarbon ring; $R^3$ is lower alkyl, lower alkenyl, lower fluoroalkyl, lower fluoroalkenyl, O-lower alkyl, O-lower alkenyl, O-lower acyl, O-aromatic acyl or lower cycloalkyl; $X^1$ is hydrogen or hydroxyl, or, taken with $R^3$, constitutes a bond when $R^3$ is an alkenyl group, and $X^2$ is hydrogen or hydroxyl, or, taken with $R^1$ or $R^2$, constitutes a double bond.

6. The method of claim 5, wherein said therapeutic amount is 0.01 µg/kg/day to 2.0 µg/kg/day.

7. A method of treating human prostate cancer, comprising administering to a male subject, who has prostate cancer, an effective amount of a first anticancer agent which is an active vitamin D compound to decrease or stabilize the cellular abnormal proliferative activity of the cancer, said compound or its in vivo metabolite having a VDR binding affinity substantially equivalent to the binding affinity of 1α,25-dihydroxyvitamin $D_3$ and a hypercalcemia risk substantially lower than that of 1α,25-dihydroxyvitamin $D_3$.

8. The method of claim 7, wherein said active vitamin D is administered in a mixture including a second anticancer agent selected from the group consisting of estramustine phosphate, prednimustine, cisplatin, 5-fluoro-uracil, melphalan, hydroxyurea, mitomycin, idarubicin, methotrexate, adriamycin and daunomycin.

9. A method of treating a human to alleviate the hyperproliferative cellular activity of prostatic cancer or hyperplasia, comprising administering to a human in need thereof a therapeutically effective amount of an active vitamin D compound having a hydrocarbon moiety substituted at C-24.

* * * * *